(12) United States Patent
Van Dun et al.

(10) Patent No.: US 9,926,572 B2
(45) Date of Patent: Mar. 27, 2018

(54) REVERSIBLE GENIC MALE STERILITY IN COMPOSITAE

(71) Applicant: RIJK ZWAAN ZAADTEELT EN ZAADHANDEL B.V., De Lier (NL)

(72) Inventors: Cornelis Maria Petrus Van Dun, De Lier (NL); Johannes Wilhelmus Schut, De Lier (NL); Beatrice Ingrid Lindhout, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 139 days.

(21) Appl. No.: 14/788,857

(22) Filed: Jul. 1, 2015

(65) Prior Publication Data

US 2016/0002665 A1   Jan. 7, 2016

Related U.S. Application Data

(63) Continuation-in-part of application No. PCT/EP2014/050324, filed on Jan. 9, 2014.

(30) Foreign Application Priority Data

Jan. 11, 2013 (EP) .................... 13151073

(51) Int. Cl.

| | | |
|---|---|---|
| *A01H 5/00* | (2006.01) | |
| *A01H 1/06* | (2006.01) | |
| *C12N 15/82* | (2006.01) | |
| *C07K 14/415* | (2006.01) | |
| *C12N 9/02* | (2006.01) | |
| *C12N 9/88* | (2006.01) | |
| *C12N 9/90* | (2006.01) | |
| *C12N 15/01* | (2006.01) | |
| *C12N 15/00* | (2006.01) | |

(52) U.S. Cl.
CPC .......... *C12N 15/8218* (2013.01); *A01H 1/06* (2013.01); *C07K 14/415* (2013.01); *C12N 9/0004* (2013.01); *C12N 9/88* (2013.01); *C12N 9/90* (2013.01); *C12N 15/01* (2013.01); *C12N 15/8289* (2013.01); *C12N 15/00* (2013.01)

(58) Field of Classification Search
None
See application file for complete search history.

(56) References Cited

U.S. PATENT DOCUMENTS

2010/0115660 A1   5/2010   Wiig

FOREIGN PATENT DOCUMENTS

WO   2008/095910   8/2008

OTHER PUBLICATIONS

International Search Report dated Apr. 16, 2014, which issued during prosecution of International Application No. PCT/EP2014/050324.
H.K. Bae, et al. "Transgenic rice plants carrying RNA interference constructs of AOS (allene oxide synthase) genes show severe male sterility" Plant Breeding 129(6):647-651, Dec. 2010.
Lei Li, et al. "The Tomato Homolog of Coronatine-Insensitive1 is Required for the Maternal Control of Seed Maturation, Jasmonate-Signaled Defense Responses, and Glandular Trichome Development" The Plant Cell 16(1):126-143, Jan. 2004.
Joon-Hyun Park, et al. "A knock-out mutation in allene oxide synthase results in male sterility and defective wound signal transduction in *Arabidopsis* due to a block in jasmonic acid biosynthesis" The Plant Journal 31(1):1-12, Jul. 2002.
Paul M. Sanders, et al. "The *Arabidopsis* Delayed Dehiscence1 Gene Encodes an Enzyme in the Jasmonic Acid Synthesis Pathway" The Plant Cell 12(7):1041-1061, Jul. 2000.
Annick Stintzi, et al. "The *Arabidopsis* male-sterile mutant, opr3, lacks 12-oxophytodienoic acid reductase required for jasmonate synthesis" Proceedings of the National Academy of Sciences of the United States of America 97(19):10625-10630, Sep. 2000.
John G. Turner, et al. "The Jasmonate Signal Pathway" The Plant Cell 14(Suppl):S153-S164, 2002.
Vick, et al. "Biosynthesis of Jasmonic Acid by Several Plant Species" Plant Physiol., 1984, 75:458-461.

*Primary Examiner* — Phoenix Bui
(74) *Attorney, Agent, or Firm* — Vedder Price P.C.; Thomas J. Kowalski; Deborah L. Lu

(57) ABSTRACT

The present invention relates to plants of the Compositae family exhibiting a reversible genic male sterility trait, characterized in that the genic male sterility is caused by a reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10, 11-reductase, or their functional homologues.

3 Claims, 2 Drawing Sheets

REVERSIBLE GENIC MALE STERILITY IN COMPOSITAE

RELATED APPLICATIONS AND INCORPORATION BY REFERENCE

This application is a continuation-in-part application of international patent application Serial No. PCT/EP2014/050324 filed 9 Jan. 2014, which published as PCT Publication No. WO 2014/108471 on 17 Jul. 2014, which claims benefit of European patent application Serial No. 13151073.7 filed 11 Jan. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Sep. 23, 2015, is named 43104002218_SL.txt and is 3,798 bytes in size.

FIELD OF THE INVENTION

The present invention relates to Compositae plants exhibiting a reversible genic male sterility trait. The invention further relates to cells, seeds and progeny of such plants, and to propagation material for obtaining the plants. The invention also relates to markers and the use of the markers for identifying the presence of the reversible genic male sterility trait.

BACKGROUND OF THE INVENTION

In commercial plant breeding the production of hybrid seed is very important. Plants grown from hybrid seed are generally very uniform, and they benefit from heterosis (hybrid vigor), which can lead to a significant increase in yield and/or performance when compared to the parental lines of the hybrid, or to outcrossing (open-pollinated) lines. Typically the parental lines used for hybrid seed production are inbred, which implies that their genomes are largely homozygous. The combination of two largely homozygous genomes into a hybrid leads to a high degree of heterozygosity, if both parental lines were genetically unrelated or not closely related.

Efficient hybrid seed production in plant species that are able to self-fertilize requires adequate measures to prevent self-fertilisation of the plants on which hybrid seeds are to be produced. Various strategies have been developed to achieve this, and to obtain an efficient hybrid seed production setup. However, the complexity and amount of labor required for each of these strategies varies greatly.

A strategy that naturally occurs in certain plant species is the physical separation of male and female reproductive organs in separate flowers, either on separate plants (dioecious species) or on the same plant (monoecious species). This system naturally promotes outcrossing, and it can be easily taken advantage of for hybrid seed production.

Another natural strategy is self-incompatibility, which has e.g. been extensively studied in *Brassica* species. In this case, pollen is physically unable to fertilize egg cells from the same plant. The precise mechanism of the incompatibility interaction can differ. Either pollen hydration or germination is prevented, or pollen tube growth through the style is inhibited by the female tissues, or the pollen tube is not attracted to ripe ovules, or the sperm nuclei are unable to merge with the egg cell nucleus to form a viable zygote. Again, this naturally occurring system is very efficient and useful for preventing self-fertilisation, and for promoting outcrossing.

Another method for preventing selfing, which is typically used in e.g. maize, is the mechanical elimination of all male flowers (detasseling). The only flowers remaining on the plant are female, and these can be manually pollinated with pollen from a selected paternal line, in order to obtain ears with exclusively hybrid kernels.

In plant species with hermaphroditic flowers (producing both ovules and pollen grains within the same flower), a common strategy for preventing selfing is emasculation by mechanical removal of anthers and/or pollen prior to anthesis. When the anthers are mechanically removed before the pollen grains are released from the loculi and/or before the filament has extended far enough to match the height of the stigma, selfing is efficiently prevented. Subsequently the female reproductive parts of the emasculated flower are allowed to mature normally, after which pollen grains from a selected father plant can be deposited on the stigma, in order to obtain exclusively hybrid seeds from the cross. Especially for commercial-scale applications this method is however very labor-intensive and not 100% reliable: if anthers are removed in a slightly too late developmental stadium or if one anther is accidentally not removed, this can lead to a mixed seed set, consisting of hybrid and maternal seeds. This results in non-uniformity of the commercial seed batch, which is undesired for customers who expect uniform and consistently superior seeds, and it brings inbred mother lines of hybrid varieties into commerce, which is undesired for the breeding company. A 100% reliable hybrid system is therefore desirable.

Another approach is to induce male sterility by means of chemicals. This so-called male gametocide can be achieved by treatment with e.g. gibberellins (in rice and maize), sodium methyl arsenate (in rice), or maleic acid (in wheat and onion). Disadvantages of this approach are the fact that this male sterility is not inheritable as it does not result from a genetic determinant present in the plant's genome, and that chemical treatment is labor intensive and not 100% reliable.

Another category of mechanisms through which selfing can be prevented, is termed genetic male sterility. Here three different approaches can be distinguished: genetic-engineered male sterility (transgenic MS), cytoplasmic male sterility (CMS) and genic male sterility (GMS). Transgenic MS may comprise all approaches that use a transgene to ensure that pollen grains are unable to fertilize ovules, and that either lead to the death of pollen grains prior to anthesis, or to the dysfunctionality of pollen grains at anthesis. A well-known example is the reversible Barnase/Barstar system, wherein the Barnase enzyme is transgenically expressed in the tapetum, which leads to pollen sterility.

However, when the Barstar protein is co-expressed in the tapetum, it blocks Barnase activity and restores pollen fertility (Mariani et al., 1990, *Nature* 347: 737-41).

Cytoplasmic male sterility (CMS) is a type of sterility that is under control of extra-nuclear, cytoplasmic factors, more precisely of plastid origin. Usually mutations in the mitochondrial genome underlie CMS, and they typically inherit in a maternal fashion. Routine hybrid seed production with CMS lines requires the use of maintainer and restorer lines, which complicates the process and increases the costs and time required for commercial hybrid seed production.

Genic male sterility (GMS) encompasses a nuclear influence on male fertility, in contrast to cytoplasmic influences which are caused by organellar factors. Due to e.g. a mutation in a nuclear gene the plant does not produce viable and/or functional pollen grains or male spores, and/or it is unable to disperse its pollen due to e.g. non-dehiscence of its anthers.

The Asteraceae family—also known as the Compositae family—is one of the largest extant plant families. It may comprise various commercially important crop plants, such as sunflower (*Helianthus*), lettuce (*Lactuca*), endive, witloof and radicchio (*Cichorium*), artichoke (*Cynara*), and many ornamental plants such as *Chrysanthemum, Tagetes, Gerbera* and *Zinnia*.

In the Compositae family only few types of male sterility have been developed for commercial exploitation and hybrid seed production. Emasculation is very difficult in this family, due to the composite nature of the inflorescences. In e.g. endive and witloof, self-pollinaton is normally prevented by spraying an inflorescence with water, to flush away the pollen. Timing is crucial, because this spraying needs to be done immediately after opening of the anthers, before the stigma splits into two curving parts that protrude beyond the anthers. After spraying the inflorescence has to be blown dry and has to be allowed to develop further, before pollen grains from a selected father can be deposited onto the stigma. It is critical to choose the optimal moment for spraying with water: if pollen are removed too late some self-pollination will already have occurred, and if pollen are removed before the anthers are fully opened, pollen grains will remain present and may cause self-pollination at a later stage. Every day there is only a limited time window during which this spraying can be done, and its timing depends strongly on light and temperature conditions. The development of an efficient, reversible male sterility system in the Compositae family would thus greatly facilitate breeding in crop species belonging to this family.

Hybrid sunflowers are available and can be produced using various methods described above. However for e.g. endive a hybrid system is not yet available at all, and a major problem is the very limited genetic variation within this cultivated crop. If an efficient hybrid system would be available for endive, this could be used to increase the genetic variation, as well as provide additional benefits through heterotic effects. Interspecific crosses with e.g. witloof (*Cichorium intybus*) are possible, and these could be used to introduce foreign genetic material into endive germplasm, but this would lead to complications at the genetic level, namely the fact that the resulting progeny would no longer be purely endive, but a mixture of endive and witloof.

In witloof a recessive GMS trait has previously been created through a transposon insertion in a homologue of the DYT1 gene of *Arabidopsis* (Quillet et al., 2011, Cloning and characterization of nuclear male sterility 1 (nms1) in chicory). However, in practice it is very difficult to transfer this transposon-based trait to endive (*Cichorium endivia*). Also, although the transposon may spontaneously be excised from the DYT1 gene homologue and thus potentially restore fertility, a researcher is not able to easily, predictably and consistently reverse this male sterility trait in witloof whenever he wishes to do so.

CMS has also been created in witloof, by combining the nuclear genome from *C. intybus* with cytoplasm from sunflower (*Helianthus annuus*). However, again this is not a reversible male sterility, and the perpetuation of the trait requires maintainer and restorer lines.

In lettuce, male sterility has been described in the prior art, and pollination for obtaining hybrid seeds can e.g. be achieved with bees (U.S. Pat. No. 7,569,743). Dominant GMS is available (resulting from the MS7 mutation), as well as CMS (through combination of the nuclear genome of *Lactuca sativa* with the cytoplasm of sunflower). However, none of these traits is reversible, and it thus requires more efforts to maintain the male-sterile mother lines in any of those cases.

One could imagine a transgenic approach to obtain reversible male sterility in Compositae plants, e.g. with the Barnase/Barstar system, but such transgenic plants would have a uregulated" status, which is undesired in e.g. the European market, and this would necessitate large extra deregulation expenses to obtain market approval. The cost for bringing hybrid seeds resulting from the use of such a transgenic reversible male-sterile Compositae plant to the market would thus become quite high.

It is therefore an object of the present invention to provide a reversible male sterility system in Compositae plants for the efficient and convenient production of hybrid seeds.

In the research leading to the present invention it was found that Compositae plants can be rendered male-sterile through a loss-of-function mutation in the OPR3 gene, and that this male sterility can be reversed by the application of methyl jasmonate (MeJA) and/or jasmonic acid or other jasmonic acid derivatives to flower buds.

The OPR3 gene encodes the 12-oxophytodienoic acid reductase protein, which is a key enzyme in the biosynthesis of the phytohormone jasmonic acid. In the model plant species *Arabidopsis thaliana* jasmonic acid is required for male fertility, and mutations in the *Arabidopsis* OPR3 gene were reported to cause male sterility. Male fertility could be restored by treating flower buds with methyl jasmonate (Stintzi and Browse, 2000; *Proc. Natl. Acad. Sci. USA* 97: 10625-10630). However, this observation in *Arabidopsis* is apparently not by definition valid for other plant species. In tomato, for example, jasmonic acid is required for the maternal control of seed maturation, but not for male fertility (Li et al., 2004; *Plant Cell* 16: 126-143). In maize, defects in jasmonate signalling and biosynthesis affect female fertility, not male fertility (Lyons et al., 2013; *Plant Cell Rep.* 32: 815-827). These reports clearly indicate that the jasmonic acid pathway regulates distinct developmental processes in different plant species.

It is surprising that targeting functional homologues of the OPR3 gene in a plant family other than the Brassicaceae actually leads to reversible male sterility, especially since from a phylogenetic point of view the Compositae family is closer related to the Solanaceae family (such as tomato, in which jasmonic acid is not involved in male fertility) than to the Brassicaceae family (such as *Arabidopsis*). Among the eudicots, the Compositae and Solanaceae families both belong to the Asterids clade, whereas the Brassicaceae family belongs to the Rosids clade. The skilled person would not be able to establish, without undue burden, in which plant families other than the Brassicaceae or Solanaceae, which have been investigated in the prior art, the jasmonic acid pathway may or may not regulate male fertility.

Citation or identification of any document in this application is not an admission that such document is available as prior art to the present invention.

SUMMARY OF THE INVENTION

Reversible genic male sterility provides a great advantage over non-reversible genic male sterility. When the genic male sterility trait performs in a reliable and consistent manner, a male-sterile mother plant will exclusively produce hybrid seeds, when pollinated with pollen from a selected father plant (e.g. through manual pollination or insect pollination), without a need for emasculation or other means to induce male sterility. In addition, it is very easy to propagate and maintain the male-sterile mother plant: upon a specific treatment, the male sterility can be reversed and the mother plant becomes entirely fertile, and it can thus self-fertilize to produce inbred seeds that are homozygous for the said genic male sterility trait. In cases of non-reversible genic male sterility this is not possible, and it is more difficult to maintain the genic male sterility trait from generation to generation.

This invention relates to a plant of the Compositae family (also known as the Asteraceae family) exhibiting a reversible genic male sterility trait, characterized in that the genic male sterility trait is caused by the reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10,11-reductase (OPR3), or their functional homologues.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of *Lactuca sativa* which may comprise a genetic determinant of the invention which leads to reversible genic male sterility that can be reversed by the application of jasmonic acid and/or one or more jasmonic acid derivatives, in particular methyl jasmonate, were deposited with NCIMB Ltd, Ferguson Building, Craibstone 5 Estate, Bucksburn, Aberdeen AB21 9YA, UK on Oct. 8, 2012 under deposit accession number NCIMB 42060. All seeds of this deposit may comprise the genetic determinant of the invention in a homozygous state.

Seeds of *Cichorium endivia* which may comprise a genetic determinant of the invention which leads to reversible genic male sterility that can be reversed by the application of jasmonic acid and/or one or more jasmonic acid derivatives, in particular methyl jasmonate, were deposited with NCIMB Ltd, Ferguson Building, Craibstone 5 Estate, Bucksburn, Aberdeen AB21 9YA, UK on 21 Dec. 2012 under deposit accession number NCIMB 42092. About 50% of the seeds of this deposit comprise the genetic determinant of the invention in a homozygous state, and about 50% of the seeds of this deposit may comprise the genetic determinant of the invention in a heterozygous state.

The Deposits with NCIMB, under deposit accession numbers 42060 and 42092 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

Panel A shows an inflorescence from a wild-type lettuce plant after flowering (left-hand side), as compared to an inflorescence from a lettuce plant of the invention after flowering (right-hand side). Neither of the plants has been pollinated with pollen from another lettuce plant. The wild-type lettuce plant is fully fertile, and it has produced seeds through selfing. The lettuce plant of the invention, in contrast, which has not been treated with jasmonic acid and/or one or more jasmonic acid derivatives, shows a complete absence of seeds in the inflorescence. This demonstrates that the presence of the reversible genic male sterility trait of the invention makes the plant completely self-sterile. Panel B illustrates the effect of treatment with jasmonic acid and/or jasmonic acid derivatives on the fertility of a reversible genic male-sterile lettuce plant of the invention. The inflorescence was treated with methyl jasmonate ("MeJA") during its development, and has produced seeds through selfing.

Figure 2:
Figure 2:
Figure 2:
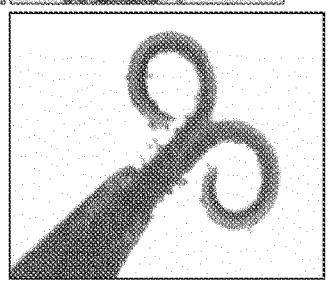
Figure 2:
Figure 2:

FIG. 2: Reversible male sterility in endive.

Panel A shows the flower and stamens of a wild-type endive plant (upper 2 pictures), which has a blue color (grey in the picture) and normal pollen production, as compared to a typical flower of a reversible genic male-sterile endive plant of the invention, which has a pale flower color (white in the picture) and less pollen production (lower 2 pictures). The pollen grains produced by the endive plants of the invention were not functional. Panel B illustrates the effect of treatment with jasmonic acid and/or jasmonic acid derivatives on the fertility of a reversible genic male-sterile endive plant of the invention. The left-hand picture shows an untreated flower of a plant of the invention, which is white in color and male-sterile. The right-hand picture shows a plant of the invention with in the centre a flower that has been treated with methyl jasmonate at an early stage of its development. Its color has changed to blue (grey in the picture), and it has become male-fertile. The flower above the centre flower is not treated and is still pale (white in the picture).

DETAILED DESCRIPTION OF THE INVENTION

This invention relates to a plant of the Compositae family (also known as the Asteraceae family) exhibiting a reversible genic male sterility trait, characterized in that the genic male sterility trait is caused by the reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10,11-reductase (OPR3), or their functional homologues.

The aforementioned genes encode the enzymes that constitute the jasmonic acid biosynthetic pathway in plants. Lipoxygenase converts α-linolenic acid to 13-hydroperoxylinoleic acid, which is further converted to 12,13-epoxyoctadecatrienoic acid by the action of allene oxide synthase. The latter molecule is the substrate of allene oxide cyclase, by which it is converted into (9S,13S)-12-oxo-phytodienoic acid, which can be further processed into 3-oxo-2(2'[Z]-pentenyl)-cyclopentane-1-octanoic acid by the enzymatic action of the 12-oxo-phytodienoic acid-10,11-reductase (OPR3) enzyme. Three cycles of β-oxidation are subsequently required to convert the 3-oxo-2(2'[Z]-pentenyl)-cyclopentane-1-octanoic acid molecule into (3R, 7S)-jasmonic acid.

Functional homologues of the aforementioned genes are genes that encode proteins that perform essentially the same biological function as the proteins encoded by the aforementioned genes, in the same organism or in another organism. A functional homologue that is present in the same organism as the gene to which a biological function has been ascribed (e.g. 12-oxo-phytodienoic acid-10,11-reductase activity) may be regarded as a paralogous gene. Typically, such a functional homologue would have originated from the duplication of the entire genome, of a genome fragment or of a single gene, followed by its retention in the genome as an active gene. This situation at least initially leads to functional redundancy of the two paralogous genes, which may ultimately, in the course of evolution, lead to the loss or elimination of one of the functionally redundant paralogues, or to e.g. the acquisition of a new function by one of the paralogues, e.g. by changes in its spatiotemporal expression profile during the organism's lifecycle. In many plant species, gene- and/or genome-duplications have resulted in the presence of multiple copies of genes.

A functional homologue that is present in another organism may be regarded as an orthologous gene. It performs essentially the same function in the other organism, when it functions in the same biological process that has been conserved across the species-boundaries. It may of course also have one or more paralogues in that other organism, which may be completely or partly functionally redundant.

Functional homology between genes may e.g. be demonstrated by using a paralogous or orthologous gene to genetically complement an organism carrying a loss-of-function mutation in the gene to which the paralogous and/or orthologous gene is homologous. If the transgenic expression of the paralogous or orthologous gene (under control of a suitable promoter, e.g. the original, endogenous promoter of the mutated gene) is sufficient to bypass or overcome the effects of the loss-of-function mutation, this would convincingly prove the functional homology between the original gene and its paralogue or orthologue. Another approach to demonstrate functional homology is the in vitro assessment of protein functionality, e.g. by means of enzyme assays. If two proteins can be shown to have essentially the same biological activity (e.g. enzyme activity, DNA-binding activity, etc.), they may be regarded as functional homologues.

Functional paralogues and functional orthologues of the aforementioned target genes in members of the Compositae family, involved in endogenous jasmonic acid production (such as OPR3) or inherently suitable to fulfill such a function when expressed in suitable tissues at suitable developmental time points, are also intended to fall under the scope of this invention.

In one embodiment the male sterility in plants of the invention can be reversed by the application of one or more jasmonic acid derivatives, in particular methyl jasmonate. Methyl jasmonate (MeJA) is a volatile derivative of jasmonic acid from which it can be converted in planta in a reaction catalysed by the S-adenosyl-L-methionine:jasmonic acid carboxyl methyltransferase enzyme.

In another embodiment jasmonic acid can be used.

Conditional and controlled reversibility of the male sterility phenotype is very useful, because it allows the easy maintenance of male-sterile plants of the invention across successive generations. The application of one or more jasmonic acid derivatives, in particular methyl jasmonate, renders the male-sterile plants of the invention entirely fertile (both male- and female-fertile), and capable of self-fertilisation. In this manner the male sterility trait of the invention can be conveniently transmitted to the next generation, without the need for e.g. restorer or maintainer lines.

The application of jasmonic acid and/or one or more jasmonic acid derivatives, in particular methyl jasmonate, can be done in various ways, such as spraying them in an aqueous solution or directly applying them with a brush onto young flower buds in an aqueous solution, or on a regular basis adding them to the water or substrate provided to the plants, such that they are taken up by the plant and distributed therein in a systemic manner.

In one embodiment the interfering with the one or more target genes involved in endogenous jasmonic acid production (such as OPR3) consists of preventing transcription thereof. Preventing transcription can for example be achieved by means of RNA oligonucleotides, DNA oligonucleotides or RNAi molecules directed against the target gene promoter, or preferably by means of the expression of a negatively acting transcription factor acting on the target gene promoter.

In another embodiment the interfering with the one or more target genes involved in endogenous jasmonic acid production (such as OPR3) consists of destabilising the target gene mRNA or transcript, preferably by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides. Such methods for destabilising mRNA or transcripts are well-known to the person skilled in the art. For example, in the case of RNAi, which is generally mediated by dsRNA molecules of 21 and 22 nucleotides, nucleic acid molecules of at least 38 base pairs that are complementary to (part of) the target gene mRNA or transcript are recommended as a template for gene silencing, although complementary fragments of at least 150 or 200 base pairs are most commonly used as a template for gene silencing (Elbashir et al., *Genes Dev.* 2001; 15: 188-200).

In another embodiment the interfering with the one or more target genes involved in endogenous jasmonic acid production (such as OPR3) consists of inhibiting the target gene expression product, preferably by means of the expression product(s) of one or more dominant-negative nucleic acid constructs, or preferably by means of one or more chemical compounds.

A dominant-negative mutation (or antimorphic mutation) typically changes the properties of the gene product such that it antagonises the functioning of the wild-type version of the protein. Phenotypically the organism behaves as though it has a dominant or semi-dominant loss-of-function mutation in the encoding gene, for example if the dominant-negative version of a protein prevents the formation of functional protein complexes (e.g. if due to a premature stop-codon one or more C-terminal domains are missing, that are important for interaction of the protein with other proteins), or if it irreversibly binds a substrate instead of converting it to the normal reaction product(s) (e.g. in case of an enzyme), or if its activity cannot be properly regulated by the cellular machinery (e.g. when the dominant-negative mutation destroys a phosphorylation site), etc.

Chemical compounds, on the other hand, may be used to interfere with the normal functioning of a protein, for example by mimicking the substrate of an enzyme and irreversibly binding to the active site of the enzyme. Chemical inhibitors may occur in nature, or they may be identified by screening chemical libraries. Often chemical inhibitors are structural analogues of the natural substrate(s) of the protein whose function they are intended to inhibit.

In yet another embodiment the interfering with the one or more target genes involved in endogenous jasmonic acid production (such as OPR3) consists of the introduction of one or more mutations into the target gene, leading to perturbation of its biological function. The one or more mutations are preferably introduced randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements. The one or more mutations may also be introduced specifically by means of homologous recombination or oligonucleotide-based mutation induction. The techniques for introducing mutations into a genome are well known in the art.

Examples of mutations that perturb the biological function of the one or more target genes involved in endogenous jasmonic acid production (such as OPR3) are mutations that give rise to premature stop-codons, frame shifts or amino acid changes in the encoded protein. Premature stop-codons typically lead to the expression of a truncated version of the encoded protein. Depending on the mutation's position in the coding sequence, a truncated version of a protein may lack one or more domains that are essential to perform its function and/or to interact with substrates or with other proteins, and/or it may lack the ability to fold properly into a functional protein.

Frame shift mutations are caused by the introduction or deletion of one or more base pairs in a DNA sequence encoding a protein. When the number of inserted or deleted base pairs at a certain position is not a multiple of 3, the triplet codons encoding the individual amino acids of the protein sequence become shifted relative to the original open-reading frame, and the encoded protein sequence changes dramatically. Protein translation will result in an entirely different amino acid sequence than that of the originally encoded protein, and often a frame shift also leads to a premature stop-codon in the open reading frame. The overall result is that the encoded protein no longer has the same biological function as the originally encoded protein.

Amino acid changes in an encoded protein sequence arise when the mutation of one or more base pairs in the coding sequence results in an altered triplet codon, encoding a different amino acid. Due to the redundancy of the genetic code not all point mutations lead to amino acid changes. Such mutations are termed usilent mutations". Some amino acid changes are uconservative", i.e. they lead to the replacement of one amino acid by another amino acid with comparable properties, such that the mutation is unlikely to dramatically change the folding of the mature protein, or influence its function. Especially non-silent, non-conservative amino acid changes (whereby an amino acid is replaced by another amino acid with different properties) in domains that play a role in substrate-recognition, the active site of enzymes, interaction domains or in major structural domains (such as transmembrane helices) may partly or completely destroy the functionality of an encoded protein, without thereby necessarily affecting the expression level of the encoding gene.

Mutations in the promoter sequence of a target gene involved in endogenous jasmonic acid production (such as OPR3) may also perturb the biological function of the encoded protein, as they may lead to a complete lack of transcription of the gene, or to a significantly decreased and biologically inadequate level of transcription. Mutations in splice sites may also perturb the biological function of the encoded protein, because if a splice site is destroyed by a mutation, the amino acid sequence encoded in the mature mRNA transcribed from the gene will not be correct, and it may easily contain frame shifts and/or premature stop-codons. In either case, the protein sequence translated from such an mRNA will not be identical to the originally encoded protein sequence, which will most likely have serious consequences for the biological functionality of the translated protein.

This invention also relates to plants of the genus *Lactuca*, exhibiting a reversible genic male sterility trait according to the present invention. In one embodiment, the plants belong to the species *Lactuca sativa*, and the reversible male sterility trait is caused by a genetic determinant, the presence of which genetic determinant can be identified by a molecular marker characterized by SEQ ID No. 1, and wherein the said genetic determinant is as present in the genome of plants grown from seed of which a representative sample was deposited with the NCIMB under accession number NCIMB 42060. Said genetic determinant is a single nucleotide polymorphism (SNP), and the person skilled in the art is familiar with experimental methods to detect SNPs in a genome. Such methods include, among others, DNA-sequencing, TaqMan®, SNP-arrays, Invader®, KASPar™, etc.

This invention also relates to *Lactuca* plants exhibiting a reversible genic male sterility trait, obtainable by crossing a first *Lactuca* plant with a second *Lactuca* plant, wherein one of the said plants is grown from seeds of which a representative sample was deposited with the NCIMB under accession number NCIMB 42060, or a progeny plant thereof, and selecting, preferably in the F2 generation, for plants that exhibit a reversible genic male sterility trait.

Alternatively, selection can already be done in the F1 generation by means of a molecular marker detecting the SNP of SEQ ID No. 1.

This invention further relates to seed of a *Lactuca* plant exhibiting a reversible genic male sterility trait, wherein the plant that can be grown from the seed may comprise the genetic determinant that can be identified by a molecular marker characterized by SEQ ID No. 1, and wherein the said genetic determinant is as present in the genome of plants grown from seed of which a representative sample was deposited under accession number NCIMB 42060.

This invention further relates to progeny of a *Lactuca* plant exhibiting a reversible genic male sterility trait, which may comprise the genetic determinant that can be identified by a molecular marker characterized by SEQ ID No. 1, and wherein the said genetic determinant is as present in the genome of plants grown from seed of which a representative sample was deposited under accession number NCIMB 42060.

Such progeny can be produced by sexual or vegetative reproduction of a plant of the invention or a progeny plant thereof. The progeny plant displays the reversible genic male sterility trait in the same or in a similar way as the plant of which representative seed was deposited under accession number NCIMB 42060. This means that such progeny has the same characteristics as claimed for lettuce plants of the invention.

As used herein, the word "progeny" is intended to mean the offspring or the first and all further descendants from a cross with a plant of the invention that shows the reversible genic male sterility trait. Progeny of the invention may comprise descendants of any cross with a plant of the invention that carries the reversible genic male sterility trait. Such progeny is for example obtainable by crossing a first lettuce plant with a second lettuce plant, wherein one of the lettuce plants was grown from seeds of a plant of the invention, representative seeds of which were deposited under NCIMB accession number 42060, but it can also be the progeny of any other lettuce plant carrying the reversible genic male sterility trait as present in seeds of deposit NCIMB 42060.

It is understood that a parent plant that provides the trait of the invention is not necessarily a plant grown directly from the deposited seeds. The parent can also be a progeny plant from the seed, or a progeny plant from seeds that are identified to have (or to have acquired) the trait of the invention by other means. In one embodiment, the invention relates to lettuce plants that carry the trait of the invention and that have acquired the said trait by introduction of the genetic information that is responsible for the trait from a suitable source, either by conventional breeding, or genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

In one embodiment, the source from which the genetic information is acquired is formed by plants grown from the deposited seeds, or by sexual or vegetative descendants therefrom.

"Progeny" also encompasses plants that carry the trait of the invention which are obtained from other plants of the invention by vegetative propagation or multiplication.

This invention also relates to propagation material suitable for producing a *Lactuca* plant exhibiting a reversible genic male sterility trait, which may comprise the genetic determinant that can be identified by a molecular marker characterized by SEQ ID No. 1, and wherein the said genetic determinant is as present in the genome of plants grown from seed of which a representative sample was deposited under accession number NCIMB 42060.

In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and tissue cultures of regenerable cells, parts of the plant that are suitable for preparing tissue cultures, in particular leaves, pollen, embryos, cotyledons, hypocotyls, meristematic cells, root tips, anthers, flowers, seeds and stems.

The invention further relates to a lettuce plant grown or regenerated from the said propagation material of a plant of the invention, which plant exhibits the reversible genic male sterility trait of the invention.

The invention further relates to a cell of a lettuce plant of the invention, which cell may comprise a genetic determinant which leads to reversible genic male sterility, wherein the said genetic determinant is as present in a lettuce plant, representative seeds of which were deposited under NCIMB accession number 42060. The said cell thus may comprise the genetic information encoding the said reversible genic male sterility trait, in particular genetic information which is substantially identical, preferably completely identical to the genetic information encoding the said reversible genic male sterility trait of the lettuce plant, representative seeds of which were deposited under NCIMB accession number 42060. Preferably, the cell of the invention is part of a plant or plant part, but the cell may also be in isolated form.

The invention also relates to a cell of a lettuce plant of the invention, which cell may comprise a genetic determinant which leads to reversible genic male sterility, and which plant is obtained by transferring the reversible genic male sterility trait as found in seeds that were deposited under NCIMB accession number 42060 into an agronomically valuable lettuce plant.

The invention further relates to seed of the lettuce plant of the invention, which seed contain in their genome the genetic information that encodes the reversible genic male sterility trait of the invention.

The invention also relates to the use of seeds that were deposited under NCIMB accession number 42060 for transferring reversible genic male sterility into another agronomically valuable lettuce plant.

The invention also relates to the use of a lettuce plant of the invention that exhibits reversible genic male sterility due to the presence, in the genome of the plant, of the reversible genic male sterility trait as found in seeds that were deposited under NCIMB accession number 42060 as a crop.

The invention further relates to the use of a lettuce plant of the invention that exhibits reversible genic male sterility due to the presence, in the genome of the plant, of the reversible genic male sterility trait as found in seeds that were deposited under NCIMB accession number 42060 as a source of seed.

The invention also relates to the use of a lettuce plant of the invention that exhibits reversible genic male sterility due to the presence, in the genome of the plant, of the reversible genic male sterility trait as found in seeds that were deposited under NCIMB accession number 42060 as a source of propagating material.

The invention also relates to the use of a lettuce plant of the invention that exhibits reversible genic male sterility due to the presence, in the genome of the plant, of the reversible genic male sterility trait as found in seeds that were deposited under NCIMB accession number 42060 for consumption.

The invention also relates to harvested leaves of lettuce plants of the invention, to food products which may comprise harvested leaves of lettuce plants of the invention, either in natural or in processed form, and to a container which may comprise one or more lettuce plants of the invention in a growth substrate for harvest of leaves from the lettuce plant in a domestic environment.

The invention further relates to the use of a lettuce plant of the invention in breeding to confer reversible genic male sterility.

The invention also relates to the use of the reversible genic male sterility trait as found in seeds that were deposited under NCIMB accession number 42060 for conferring reversible genic male sterility onto a *Lactuca sativa* plant.

The invention further relates to the use of a *Lactuca sativa* plant as a recipient of the reversible genic male sterility trait as found in seeds that were deposited under NCIMB accession number 42060.

In one aspect the invention relates to a method for production of a *Lactuca sativa* plant which exhibits a reversible genic male sterility trait, which may comprise
  a) crossing a plant which may comprise a genetic determinant that leads to the trait with another plant;
  b) selfing the resulting F1 for obtaining F2 plants;
  c) selecting plants that have the trait in the F2;
  d) optionally performing one or more additional rounds of selfing or crossing, and subsequently selecting for a plant which may comprise the trait of the invention.

In one aspect, the invention relates to a method for production of a *Lactuca sativa* plant which exhibits a reversible genic male sterility trait, which may comprise
  a) crossing a plant which may comprise the genetic determinant that leads to the trait with another plant;
  b) optionally backcrossing the resulting F1 with the preferred parent;
  c) selecting for plants that have the trait in the F2;
  d) optionally performing one or more additional rounds of selfing or crossing, and subsequently selecting for a plant which may comprise the trait.

The invention additionally provides a method of introducing another desired trait into a *Lactuca sativa* plant which exhibits the reversible genic male sterility trait, which may comprise:
  a) crossing a *Lactuca sativa* plant that exhibits the reversible genic male sterility trait, representative seeds of which were deposited under deposit number NCIMB 42060, with a second *Lactuca sativa* plant that may comprise a desired trait to produce F1 progeny;
  b) selecting an F1 progeny that may comprise said reversible genic male sterility trait and the desired trait;
  c) crossing the selected F1 progeny with either parent, to produce backcross progeny;
  d) selecting backcross progeny which may comprise the desired trait and the reversible genic male sterility trait; and
  e) optionally repeating steps c) and d) one or more times in succession to produce selected fourth or higher backcross progeny that may comprise the desired trait and the reversible genic male sterility trait. The invention includes a *Lactuca sativa* plant produced by this method.

In one embodiment selection for plants exhibiting the reversible genic male sterility trait is done in the F1 or any further generation by using a molecular marker characterized by SEQ ID No. 1. In another aspect selection for the trait of the invention is started in the F2 of a cross or alternatively of a backcross. Selection of plants in the F2 can be done phenotypically as well as by using the said marker which directly or indirectly detects the genetic determinant underlying the trait.

In one embodiment selection for plants exhibiting the reversible genic male sterility trait is started in the F3 or a later generation.

In one embodiment the plant which may comprise the genetic determinant is a plant of an inbred line, a hybrid, a doubled haploid, or of a segregating population.

The invention further provides a method for the production of a *Lactuca sativa* plant exhibiting the reversible genic male sterility trait by using a doubled haploid generation technique to generate a doubled haploid line which may comprise the said trait.

The invention also relates to a method for the production of a *Lactuca sativa* plant exhibiting the reversible genic male sterility trait by using a seed that may comprise a genetic determinant in its genome that leads to the reversible genic male sterility trait for growing the said *Lactuca sativa* plant. The seeds are suitably seeds of which a representative sample was deposited under deposit number NCIMB 42060.

The invention also relates to a method for seed production which may comprise growing *Lactuca sativa* plants from seeds of which a representative sample was deposited under deposit accession number NCIMB 42060, reversing the reversible genic male sterility by the application of jasmonic acid and/or one or more jasmonic acid derivatives, in particular methyl jasmonate, allowing the plants to produce seeds, and harvesting those seeds. Production of the seeds is suitably done by crossing or selfing. Crossing can e.g. be done by means of hand pollination or by employing suitable pollinating insects.

In one embodiment, the invention relates to a method for the production of a *Lactuca sativa* plant exhibiting the reversible genic male sterility trait by using tissue culture.

The invention furthermore relates to a method for the production of a *Lactuca sativa* plant exhibiting the reversible genic male sterility trait by using vegetative reproduction.

In one embodiment, the invention relates to a method for the production of a *Lactuca sativa* plant exhibiting the reversible genic male sterility trait by using a method for genetic modification to introduce in particular dominantly acting transgenes that cause the said trait into the *Lactuca sativa* plant, for example by means of RNAi, amiRNA or antisense, or dominant-negative versions of a target gene (such as OPR3), or through mutation. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant. The plant can also be genetically modified by mutation of a target gene (such as OPR3) to exhibit the male sterility trait of the invention.

The invention also relates to a breeding method for the development of *Lactuca sativa* plants that exhibit the reversible genic male sterility trait wherein germplasm which may comprise said trait is used. Representative seed of said plant which may comprise the genetic determinant and being representative for the germplasm was deposited under deposit accession number NCIMB 42060.

In a further embodiment the invention relates to a method for the production of a *Lactuca sativa* plant exhibiting the reversible genic male sterility trait wherein progeny or propagation material of a plant which may comprise the genetic determinant conferring said trait is used as a source to introgress the said trait into another *Lactuca sativa* plant. Representative seed of said plant which may comprise the genetic determinant was deposited under deposit accession number NCIMB 42060.

The invention provides preferably a *Lactuca sativa* plant exhibiting the reversible genic male sterility trait, which plant is obtainable by any of the methods herein described and/or familiar to the skilled person.

This invention also relates to the use of *Lactuca sativa* plants exhibiting a reversible genic male sterility trait as a female parent for the creation of hybrid *Lactuca sativa* seeds. The fact that *Lactuca sativa* plants of the invention are unable to self-fertilize due to male sterility (if they are not rendered male fertile by the application of one or more jasmonic acid derivatives, in particular methyl jasmonate) makes it possible to efficiently use *Lactuca sativa* plants of the invention as female parents for the efficient creation of hybrid *Lactuca sativa* plants, using pollen from other *Lactuca sativa* plants. Pollination of the plants of the invention can e.g. be achieved by means of manual pollination, or by employing suitable pollinating insects, such as bumblebees, bees or flies and placing reversible genic male-sterile *Lactuca sativa* plants of the invention alongside male-fertile *Lactuca sativa* plants that will function as father plants of the hybrid *Lactuca sativa* seeds, by providing functional pollen grains for a successful fertilisation of the reversible genic male-sterile *Lactuca sativa* plants of the invention. This invention further relates to hybrid lettuce seeds, obtainable by the use of *Lactuca sativa* plants exhibiting a reversible genic male sterility trait as a female parent.

According to a further aspect thereof the invention also relates to plants of the genus *Cichorium*, exhibiting the reversible genic male sterility trait. The genus *Cichorium* may comprise economically and agriculturally relevant crop species, such as *Cichorium endivia* (endive) and *Cichorium intybus* (witloof, radicchio), and also *Cichorium spinosum* and *Cichorium pumillum*, which can all be crossed to each other.

In one embodiment, the said plants belong to the genus *Cichorium* and in particular to the species *Cichorium endivia*, and the reversible male sterility trait is caused by a genetic determinant, which is as present in the genome of plants grown from seed of which a representative sample was deposited under accession number NCIMB 42092, in which the presence of the genetic determinant can be identified by a molecular marker characterized by SEQ ID No. 2. Said genetic determinant is a single nucleotide polymorphism (SNP), and the person skilled in the art is familiar with experimental methods to detect SNPs in a genome. Such methods include, among others, DNA-sequencing, TaqMan®, SNP-arrays, Invader®, KASPar™, etc.

This invention also relates to *Cichorium* plants, in particular *Cichorium endivia* plants, exhibiting a reversible genic male sterility trait, obtainable by crossing a first *Cichorium* plant, in particular a *Cichorium endivia* plant, with a second *Cichorium* plant, in particular a *Cichorium endivia* plant, wherein one of the said plants is grown from seeds of which a representative sample was deposited with the NCIMB under accession number NCIMB 42092, or a progeny plant thereof, and selecting, preferably in the F2 generation, for plants that exhibit a reversible genic male sterility trait.

This invention further relates to seed of a *Cichorium* plant, in particular a *Cichorium endivia* plant exhibiting a reversible genic male sterility trait, which is as present in the genome of plants grown from seed of which a representative sample was deposited under accession number NCIMB 42092, in which the presence of the genetic determinant can be identified by a molecular marker characterized by SEQ ID No. 2.

This invention further relates to progeny of a *Cichorium* plant, in particular a *Cichorium endivia* plant, exhibiting a reversible genic male sterility trait, which may comprise the genetic determinant, which is as present in the genome of plants grown from seed of which a representative sample was deposited under accession number NCIMB 42092, in which the presence of the genetic determinant can be identified by a molecular marker characterized by SEQ ID No. 2.

Such progeny can be produced by sexual or vegetative reproduction of a plant of the invention or a progeny plant thereof. The progeny plant displays the reversible genic male sterility trait in the same or in a similar way as the plant of which representative seed was deposited (NCIMB 42092). This means that such progeny has the same characteristics as claimed for endive plants of the invention.

As used herein the word "progeny" is intended to mean the offspring or the first and all further descendants from a cross with a plant of the invention that shows the reversible genic male sterility trait. Progeny of the invention may comprise descendants of any cross with a plant of the invention that carries the reversible genic male sterility trait. Such progeny is for example obtainable by crossing a first endive plant with a second endive plant, wherein one of the endive plants was grown from seeds of a plant of the invention, representative seeds of which were deposited under NCIMB accession number 42092, but it can also be the progeny of any other endive plant or another *Cichorium* plant carrying the reversible genic male sterility trait as present in NCIMB 42092.

It is to be understood that a parent plant that provides the trait of the invention is not necessarily a plant grown directly from the deposited seeds. The parent can also be a progeny plant from the seed, or a progeny plant from seeds that are identified to have (or to have acquired) the trait of the invention by other means. In one embodiment, the invention relates to endive plants that carry the trait of the invention and that have acquired the said trait by introduction of the genetic information that is responsible for the trait from a suitable source, either by conventional breeding, or genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

In one embodiment, the source from which the genetic information is acquired is formed by plants grown from the deposited seeds, or by sexual or vegetative descendants therefrom. "Progeny" also encompasses plants that carry the trait of the invention which are obtained from other plants of the invention by vegetative propagation or multiplication.

This invention also relates to propagation material suitable for producing a *Cichorium* plant, in particular a *Cichorium endivia* plant exhibiting a reversible genic male sterility trait, which may comprise a genetic determinant which is as present in the genome of plants grown from seed of which a representative sample was deposited under accession number NCIMB 42092, in which the genetic determinant can be identified by a molecular marker characterized by SEQ ID No. 2.

In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and tissue cultures of regenerable cells, parts of the plant that are suitable for preparing tissue cultures, in particular leaves, pollen, embryos, cotyledons, hypocotyls, meristematic cells, root tips, anthers, flowers, seeds and stems.

The invention further relates to a *Cichorium* plant grown or regenerated from the said propagation material of a plant of the invention, which plant exhibits the reversible genic male sterility trait of the invention.

The invention further relates to a cell of an endive plant of the invention, which cell may comprise a genetic determinant which leads to reversible genic male sterility, wherein the said genetic determinant is as present in an endive plant, representative seeds of which were deposited under NCIMB accession number 42092, in which the genetic determinant can be identified by a molecular marker characterized by SEQ ID No. 2. The said cell thus may comprise the genetic information encoding the said reversible genic male sterility trait, in particular genetic information which is substantially identical, preferably completely identical to the genetic information encoding the said reversible genic male sterility trait of the endive plant, representative seeds of which were deposited under NCIMB accession number 42092, in which the genetic determinant can be identified by a molecular marker characterized by SEQ ID No. 2. Preferably, the cell of the invention is part of a plant or plant part, but the cell may also be in isolated form.

The invention also relates to a cell of a *Cichorium* plant, in particular a *Cichorium endivia* plant of the invention, which cell may comprise a genetic determinant which leads to reversible genic male sterility, and which plant is obtained by transferring the reversible genic male sterility trait as found in seeds that were deposited under NCIMB accession number 42092 into an agronomically valuable endive plant.

The invention further relates to seeds of a *Cichorium* plant, in particular a *Cichorium endivia* plant of the invention, which seeds contain in their genome the genetic information that encodes the reversible genic male sterility trait of the invention.

The invention also relates to the use of seeds that were deposited under NCIMB accession number 42092 for transferring reversible genic male sterility into another agronomically valuable endive plant.

The invention also relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 as a crop.

The invention further relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 as a source of seed.

The invention also relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 as a source of propagating material.

The invention also relates to the use of a *Cichorium* plant, in particular a *Cichorium endivia* plant of the invention that exhibits reversible genic male sterility due to the presence, in the genome of the plant, of the reversible genic male sterility trait as found in seeds that were deposited under NCIMB accession number 42092 for consumption.

The invention also relates to harvested leaves of a *Cichorium* plant, in particular a *Cichorium endivia* plant of the invention, to food products which may comprise harvested leaves of endive plants of the invention, either in natural or in processed form, and to a container which may comprise one or more endive plants of the invention in a growth substrate for harvest of leaves from the endive plant in a domestic environment.

The invention further relates to the use of a *Cichorium* plant, in particular a *Cichorium endivia* plant of the invention in breeding to confer reversible genic male sterility.

The invention also relates to the use of the reversible genic male sterility trait as found in seeds that were deposited under NCIMB accession number 42092 for conferring reversible genic male sterility onto a *Cichorium endivia* plant.

The invention further relates to the use of a *Cichorium* plant as a recipient of the reversible genic male sterility trait as found in seeds that were deposited under NCIMB accession number 42092, in which the genetic determinant can be identified by a molecular marker characterized by SEQ ID No. 2.

In one aspect the invention relates to a method for production of a *Cichorium* plant, in particular a *Cichorium endivia* plant which exhibits a reversible genic male sterility trait, which may comprise
    a) crossing a plant which may comprise a genetic determinant that leads to the trait with another plant;
    b) selfing the resulting F1 for obtaining F2 plants;
    c) selecting plants that have the trait in the F2;
    d) optionally performing one or more additional rounds of selfing or crossing, and subsequently selecting for a plant which may comprise the trait of the invention.

It is clear that the parent that provides the trait of the invention is not necessarily a plant grown directly from the deposited seeds. The parent can also be a progeny plant from the seed or a progeny plant from seeds that are identified to have the trait of the invention by other means.

In one aspect, the invention relates to a method for production of a *Cichorium* plant, in particular a *Cichorium endivia* plant, which exhibits a reversible genic male sterility trait, which may comprise
    a) crossing a plant which may comprise the genetic determinant that leads to the trait with another plant;
    b) optionally backcrossing the resulting F1 with the preferred parent;

c) selecting for plants that have the trait in the F2;
d) optionally performing one or more additional rounds of selfing or crossing, and subsequently selecting for a plant which may comprise the trait.

The invention additionally provides a method of introducing another desired trait into a *Cichorium* plant, in particular a *Cichorium endivia* plant, which exhibits the reversible genic male sterility trait, which may comprise:
a) crossing a *Cichorium* plant, in particular a *Cichorium endivia* plant, that exhibits the reversible genic male sterility trait, representative seeds of which were deposited under deposit number NCIMB 42092, with a second *Cichorium* plant, in particular a *Cichorium endivia* plant, that may comprise a desired trait to produce F1 progeny;
b) selecting an F1 progeny that may comprise said reversible genic male sterility trait and the desired trait;
c) crossing the selected F1 progeny with either parent, to produce backcross progeny;
d) selecting backcross progeny which may comprise the desired trait and the reversible genic male sterility trait; and
e) optionally repeating steps c) and d) one or more times in succession to produce selected fourth or higher backcross progeny that may comprise the desired trait and the reversible genic male sterility trait. The invention includes a *Cichorium* plant, in particular a *Cichorium endivia* plant, produced by this method.

In one embodiment selection for plants exhibiting the reversible genic male sterility trait is done in the F1 or any further generation by using a molecular marker characterized by SEQ ID No. 2. In another aspect selection for the trait of the invention is started in the F2 of a cross or alternatively of a backcross. Selection of plants in the F2 can be done phenotypically as well as by using the said marker which directly or indirectly detects the genetic determinant underlying the trait.

Phenotypic selection can be done based on the observation of male sterility (whereby only non-functional pollen grains are formed) and/or based on the observation of flower color. When the genetic determinant underlying the trait of the invention is present in a homozygous state, this correlates with a pale flower color, when compared to plants not having the said genetic determinant, or to plants in which the said genetic determinant is present in a heterozygous state.

In one embodiment selection for plants exhibiting the reversible genic male sterility trait is started in the F3 or a later generation.

In one embodiment the plant which may comprise the genetic determinant is a plant of an inbred line, a hybrid, a doubled haploid, or of a segregating population.

The invention further provides a method for the production of a *Cichorium* plant, in particular a *Cichorium endivia* plant, exhibiting the reversible genic male sterility trait by using a doubled haploid generation technique to generate a doubled haploid line which may comprise the said trait.

The invention also relates to a method for the production of a *Cichorium* plant, in particular a *Cichorium endivia* plant, exhibiting the reversible genic male sterility trait by using a seed that may comprise a genetic determinant in its genome that leads to the reversible genic male sterility trait for growing the said a *Cichorium* plant, in particular a *Cichorium endivia* plant. The seeds are suitably seeds of which a representative sample was deposited with the NCIMB under deposit number NCIMB 42092.

The invention also relates to a method for seed production which may comprise growing *Cichorium endivia* plants from seeds of which a representative sample was deposited under deposit number NCIMB 42092, reversing the reversible genic male sterility by the application of jasmonic acid and/or one or more jasmonic acid derivatives, in particular methyl jasmonate, allowing the plants to produce seeds, and harvesting those seeds. Production of the seeds is suitably done by crossing or selfing. Crossing can e.g. be done by means of hand pollination or by employing suitable pollinating insects.

In one embodiment, the invention relates to a method for the production of a *Cichorium* plant, in particular a *Cichorium endivia* plant, exhibiting the reversible genic male sterility trait by using tissue culture.

The invention furthermore relates to a method for the production of a *Cichorium* plant, in particular a *Cichorium endivia* plant, exhibiting the reversible genic male sterility trait by using vegetative reproduction.

In one embodiment, the invention relates to a method for the production of a *Cichorium endivia* plant exhibiting the reversible genic male sterility trait by using a method for genetic modification to introgress in particular dominantly acting transgenes that cause the said trait into the *Cichorium endivia* plant, for example by means of RNAi, amiRNA or antisense, or dominant-negative versions of a target gene (such as OPR3), or through mutation. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant. The plant can also be genetically modified by mutation of a target gene (such as OPR3) to exhibit the male sterility trait of the invention.

The invention also relates to a breeding method for the development of *Cichorium* plants, in particular *Cichorium endivia* plants that exhibit the reversible genic male sterility trait wherein germplasm which may comprise said trait is used. Representative seed of said plant which may comprise the genetic determinant and being representative for the germplasm was deposited with the NCIMB under deposit number NCIMB 42092.

In a further embodiment the invention relates to a method for the production of a *Cichorium* plant, in particular a *Cichorium endivia* plant, exhibiting the reversible genic male sterility trait wherein progeny or propagation material of a plant which may comprise the genetic determinant conferring said trait is used as a source to introgress the said trait into another *Cichorium* plant, in particular another *Cichorium endivia* plant. Representative seed of said plant which may comprise the genetic determinant was deposited under deposit number NCIMB 42092.

The invention provides preferably a *Cichorium* plant, in particular a *Cichorium endivia* plant, exhibiting the reversible genic male sterility trait, which plant is obtainable by any of the methods herein described and/or familiar to the skilled person.

This invention also relates to the use of *Cichorium* plants exhibiting a reversible genic male sterility trait as a female parent for the creation of hybrid *Cichorium* seeds. The fact that *Cichorium* plants of the invention are unable to self-fertilize due to male sterility (if they are not rendered male-fertile by the application of jasmonic acid and/or one or more jasmonic acid derivatives, in particular methyl jasmonate) makes it possible to efficiently use *Cichorium* plants of the invention as female parents for the efficient creation of hybrid *Cichorium* plants, using pollen from other *Cichorium* plants. Pollination of the plants of the invention can e.g. be achieved by means of manual pollination, or by employing suitable pollinating insects, such as bumblebees, flies or bees, and placing reversible genic male-sterile *Cichorium* plants of the invention alongside male-fertile *Cichorium* plants that will function as father plants of the hybrid *Cichorium* seeds, by providing functional pollen grains for a successful fertilisation of the reversible genic male-sterile *Cichorium* plants of the invention. This invention further relates to hybrid *Cichorium* seeds, obtainable by the use of *Cichorium* plants exhibiting a reversible genic male sterility trait as a female parent.

This invention also relates to a food product, which may comprise edible parts of plants of the Compositae family, optionally in processed form, wherein the plants comprise the genetic determinant underlying the reversible genic male sterility trait of the invention. These edible parts can be leaves (e.g. in case of lettuce, endive, witloof and radicchio), or seeds (e.g. in the case of sunflower), or flowers (e.g. in the case of artichoke). The food products are preferably derived from lettuce and endive.

The word "trait" in the context of this application refers to the phenotype of the plant. In particular, the word "trait" refers to the trait of the invention, more in particular to the reversible genic male sterility trait. The term "genetic determinant" is used for the genetic information in the genome of the plant that causes the trait of the invention. When a plant shows the trait of the invention, its genome may comprise the genetic determinant causing the trait of the invention. The plant thus has the genetic determinant of the invention. The term "genetic determinant" as used herein encompasses a gene or allele. These terms are used interchangeably. A genetic determinant can be identified by the use of a molecular marker. A genetic determinant can alternatively be identified by the position on a genetic map, or by indication of the location on a linkage group or chromosome. When a genetic determinant is no longer linked to a specific molecular marker, but its position on a chromosome as defined on a genetic map is unaltered, this genetic determinant is still the same as when it was linked to the molecular marker. The genetic trait that it confers is therefore also still the same.

The "genetic trait" is the trait or characteristic that is conferred by the genetic determinant. The genetic trait can be identified phenotypically. However, also plant stages for which no phenotypic assay can be performed do carry the genetic information that leads to the genetic trait. "Trait" or "uphenotypic trait" can be used instead of "genetic trait".

It is clear that the parent that provides the trait of the invention is not necessarily a plant grown directly from the deposited seeds. The parent can also be a progeny plant from the seed or a progeny plant from seeds that are identified to have the trait of the invention by other means.

This invention also relates to the use of plants of the Compositae family which may comprise the genetic determinant underlying the reversible genic male sterility trait of the invention, or of plants produced from the seed of such plants or from propagation material of such plants, as germplasm in a breeding program for the development of Compositae plants exhibiting a reversible genic male sterility that can be reversed by the application of jasmonic acid and/or one or more jasmonic acid derivatives, in particular methyl jasmonate.

Deposits
Sequence Information

SEQ ID No. 1: Genetic SNP marker that is able to identify the presence of the genetic determinant that underlies the trait of the invention in *Lactuca sativa* plants grown from seeds that are deposited under accession number NCIMB 42060. A genomic fragment of the lettuce OPR3 gene is presented, wherein the position of the SNP which may comprise a change from C to T [C/T] is indicated as a T in bold and underlined. This SNP is present in plants grown from seeds of the said deposit.

ATGGCTGAAACACCGCCGTCTGCCGACAATCCAACTCTCTTTTCTCCATT

CAAGATGGGCAAGTTTAATCTCTCTCACAGGTCCGTTGTTTCTATCCTTT

CTTCTCTTCACTTTCTAATCATAAATCCGTCCCCCCTATAAAAGTCCTTC

AGATTTTGAGCTTGATCCAGTCTTGACCGATCACTATACCGTGTTTTGGT

TGTAGGGTGGTGTTAGCTCCGATGACGCGGTGTAGGGCGTTAAATAGCAT

ACCGAATCAAGCTCTGGTGGAGTATTACAGGCAGAGAGCAACCGCCGGTG

GGTTTCTCATCACGGAGGGGACAATGATCTCTCCTACCTCCGCCGGGTAA

TTTCGCTATTCCTTTTGTTCTTCAAGGGTGTTTTAGTAAATCAACATTCC

AACATAATTCACCGGGACAAACCATATAAAACCGCCACGTGGCAATTCTT

AGTTCCTTACATAGTGCTTTGTGGGACCTGCAGTATAGACTATTATTAAA

GTCACACCATTATTAAAGTCACATTCTCTTTATAACCACTTTATAAAGTC

TTTATAACTAAAAAATGTGTTTTTTTCGTTGTACTTTATAGTTAGATTAG

ATGCATAATGTGGATCTTATGAACCATTAAACAATGATACAAGCTACTTG

TGTTCTAAAGTTAAAGATGCCATTTTGATTCTTAATTTAAAAAACCCATT

TGGTTTAGGAATACCCCTTTATTCATCGATCATTATAAAGCCCAAATTAA

CGATCTTTCTGGTAAAAAAAACCCAATTTGGTGATCAGGTTCCCTCACG

TACCAGGTATATTTAATCAAGAACAAGTTGAAGCTTGGAAGAAAGTCGTG

GATGCAGTTCATGAAAAAGGCGCTGTGATCTTTTGTTAATTATGGCATGT

CGGCAGAGCATCCCACCAAGGTACGCTTTCTTCCATCTAAAAGTCTCAAA

ATCTCAACATTTTGATTTTTGAACCTAAATTCGAATCGAAAGTGATCATT

GTGTTGAACAAACAGTATATCAACCTAATGGGGTTGCACCAATATCATCT

ACAAGCAAACCCATATCGAAAAAATGGAGAATTTTAATGCCCGATGGGAC

CCACGCTCAATATCCAAACCCTCGACCACTCGCTACCCATGAAATACCAG

AGGTGGTGGAAGACTATCGTCTGGCAGCAATTAACGCCATTGAAGCAGGT

TTTGATGGAATCGAGATTCACGGAGCCCATGGTTATCTTCTCGATCAATT

CATGAAAGATGGCATCAATAATCGAACCGATGAATATGGTGGATCTTTAG

CAAACCGATGCAAATTCTTACTGAAAGTGGTGAAATCGATAGCTACAGCC

ATTGGTGCAGATAAAGTCGGTGTTAGAATCTCACCAGCTATTGACCATTT

AGACGCCATGGATTCTGACCCACGTAGCTTAGGGCTTGAAGTAATTGAAA

GACTGAATAAACTTCAGGTTGAATTAGGGTCAAAGTTGACTTATCTTCAT

GTGACTCAACCAAGGTACACGGCTTATGGTCAAACAGAAGCTGGAAGCCA

TGGAAGTGAAGAGGAAGTTGCTGAGTTGATGAAGATATGGAGAAGGGCAT

TTATGGGAACTTTTGTTTGTAGTGGTGGGTATACTAGAGAGCTTGGGATT

GAAGCTGTGGCTAAAGGGGATGCTGATTTGGTGGCTTATGGAAGGCTTTT

TATATCGAATCCGGATTTGGTTTTGAGACTCAAGGTTAATGCACCTTTGA

ATAGGTATGTTAGGGCTAGTTTTTATACACATGATCCTGTTGTAGGGTAC

ACTGATTACCCTTCACTTGAGAA

SEQ ID No. 2: Genetic SNP marker that is able to identify the presence of the genetic determinant that underlies the trait of the invention in *Cichorium endivia* plants grown from seeds that are deposited under NCIMB number 42092. A genomic fragment of the endive OPR3 gene is presented, wherein the position of the SNP which may comprise a change from C to A [C/A] is indicated as A in bold and underlined. The SNP is present in plants grown from seeds of the said deposit.

TCAACATCCAGATCTCCGATCCCAAGCAAATAATGGCTGAAACGACGCCG

TCTGCCGACAATCCAACCCTCTTTTCTCCGTACAAGATGGGCAAGTTCAA

TCTCTCTCACAGGGTGATCAGTTACTTTACTTCGATCCATTGTTCTCGCA

GCTTTCTGATCATACTTCATTCCCCCAGCAAAATAATTCAGAATTTGACC

TTGATCCAATTCTGTTTTTAATTCTTTTACCGATTAGTTCACCGTGTTTT

GGTTGTAGGGTGGTGTTAGCTCAGATGACGAGATGCAGG

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Reversible Male Sterility in Lettuce

A mutant lettuce plant (*Lactuca sativa*), having a mutated version of the OPR3 gene, was obtained by means of chemical mutagenesis and subsequent TILLING screening of about 3,000 M2 plants. DNA sequencing revealed the presence of a C to T mutation (CAA to TAA) in one M2 plant, leading at the protein level to the conversion of a Glutamine to a premature stop codon at position 107, and hence to the presumed expression of a truncated version of the OPR3 protein in this mutant plant.

Phenotypically this mutant lettuce plant was indistinguishable from wild-type lettuce plants, when the mutation was present in a heterozygous state. However, when the plant was self-pollinated and allowed to produce seeds, the homozygous mutant plants of the next generation showed complete male sterility. The few pollen grains that developed in such homozygous mutants were not functional. The homozygous mutant plants did not set seed when allowed to self-pollinate, but when used as the female parent in a cross, the plants were able to set seed, which demonstrated that their female fertility was not impaired. In this manner the mutation could be maintained in subsequent generations through screening of progeny plants of the selfing of a heterozygous mutant plant with a molecular marker designed to identify the presence of the causal mutation, SEQ ID No. 1, even though the homozygous mutant plants were male-sterile and failed to set seed through self-pollination.

The causal SNP mutation was detected by means of DNA-sequencing of a PCR-fragment of the OPR3 gene. First, a fragment of the lettuce OPR3 gene containing the SNP was amplified by PCR, using suitable PCR-primers that were designed based on the sequence information in SEQ ID No. 1. Subsequently, the DNA-sequence of the PCR product was determined by means of Sanger sequencing, using the following oligonucleotide as forward sequencing primer: GCTTGGAAGAAAGTCGTGGATG (SEQ ID NO:3). Of course various other techniques can also be used for the detection of the SNP in SEQ ID No. 1.

Figure 1:
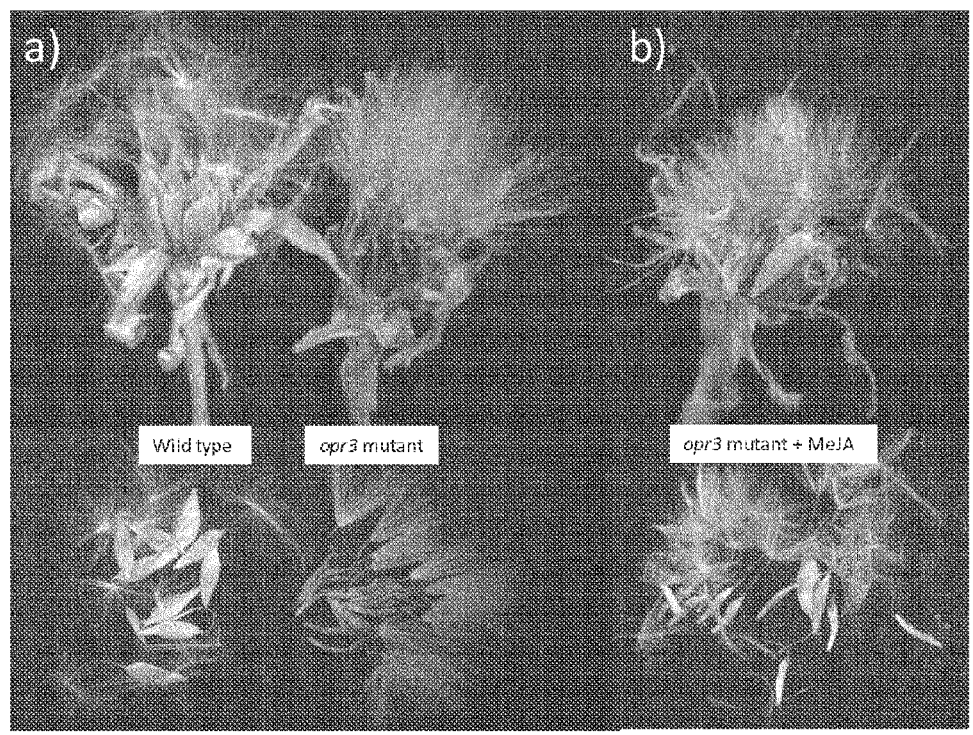
FIG. 1: Reversible male sterility in lettuce

Surprisingly, it was observed that spraying young flower buds with a 200 µM (0.2 mM) methyl jasmonate (MeJA) aqueous solution (in water plus 0.025% Zipper surfactant) was sufficient to restore male fertility in these homozygous mutants. From the early bolting stage the inflorescences were sprayed 5 times per week, for a total of 3 weeks. In contrast to mock-treated control plants—that were sprayed with an aqueous solution of 0.025% Zipper surfactant—the MeJA treated plants produced seeds in a subset of their flowers, being the flowers that had received an effective MeJA dose at the appropriate developmental stage (FIG. 1).

The seeds that were produced by the homozygous mutant plants treated with MeJA were all homozygous for the mutation, as could be demonstrated by use of a molecular marker detecting the causal mutation (SEQ ID No. 1).

Example 2

Transfer of the Reversible Male Sterility Trait to Another Lettuce Plant

Lettuce plants of the invention (of the deposit, NCIMB 42060) were crossed with wild-type (WT) lettuce plants, which do not carry the trait of the invention. The resulting F1 plants from this cross had the same phenotype as the WT plant, i.e. they displayed normal fertility. Nevertheless, the presence of the trait of the invention in a heterozygous state could be detected in all F1 plants by means of a molecular marker. The Single Nucleotide Polymorphism (SNP) that can be used for this purpose is presented as SEQ ID No. 1. This molecular marker can be used to identify the presence of the genetic determinant that underlies the trait of the invention in lettuce plants grown from seeds as deposited under NCIMB number 42060.

In the F2 generation the trait of the invention is segregated in a manner that corresponds with a monogenic recessive inheritance. The trait of the invention could be introduced into a wild-type lettuce plant by crossing the wild-type plant with a plant of the invention and selecting for the desired phenotype, by selection on male sterility and/or the presence of the molecular marker in a homozygous state. The latter method of detection has the advantage that plants of the invention can be identified at a young developmental stage, long before they start flowering. This enables the confident selection of desired plants (carrying the trait of the invention) at the seedling stage, which allows for a more efficient use of plant growth facilities.

The wild-type lettuce plant into which the trait of the invention can be introduced can be a lettuce plant of any leaf type, any form or any color.

In the F2 generation the male sterility trait was also reversible. The addition of jasmonic acid and/or one or more jasmonic acid derivatives, in particular methyl jasmonate, was sufficient to restore male fertility, as described in Example 1.

Example 3

Reversible Male Sterility in Endive

A mutant endive plant (*Cichorium endivia*), having a mutated version of the OPR3 gene, was obtained by means of chemical mutagenesis and subsequent TILLING screening of about 10,000 M2 plants. DNA sequencing revealed the presence of a C to A mutation in exon 2 (CCG to CAG) in one M2 plant, leading at the protein level to a Proline to Glutamine amino acid change at position 76.

Phenotypically this mutant endive plant was indistinguishable from wild-type endive plants, when the mutation was present in a heterozygous state. However, when the plant was self-pollinated and allowed to produce seeds, the homozygous mutant plants of the next generation showed male sterility, along with a pale flower color (almost white, compared to the blue color of wild-type flowers of this endive line). The pollen grains that developed in such homozygous mutants were unable to germinate and therefore dysfunctional. When used as the female parent in a cross, the plants were able to set seed, which demonstrated that their female fertility was not impaired. In this manner the mutation could be maintained in subsequent generations, even though the homozygous mutant plants were male-sterile and failed to set seed through self-pollination.

Surprisingly, it was observed that spraying young flower buds on a daily basis—throughout the entire flowering stage of the plant, which lasted about 3.5 months—with a MeJA solution had a dramatic effect on the mutant flowers that developed from the treated flower buds (an aqueous solution of 200 µM (0.2 mM) MeJA with 0.025% Zipper surfactant). Instead of developing into flowers with a pale color, as was the case for untreated or mock-treated flower buds (treated with an aqueous solution of 0.025% Zipper surfactant), the treated flower buds developed into blue flowers. Blue was the wild-type flower color in this endive background. In addition, the flowers that developed from MeJA-treated flower buds produced viable, functional pollen and were able to set seed through self-pollination, whereas control plants sprayed with an aqueous solution of 0.025% Zipper surfactant remained male-sterile and hence devoid of seeds.

Other application methods (other than spraying) of jasmonic acid and/or one or more jasmonic acid derivatives, in particular methyl jasmonate, had comparable effects, such as "painting" a MeJA solution onto the surface of young flower buds with a fine brush.

This experiment demonstrated that the male sterility that was caused by the opr3 mutation in endive could be overcome by the application of MeJA. The seeds that were produced by selfing of the homozygous mutant plants treated with MeJA were all homozygous for the mutation. Jasmonic acid or other derivatives thereof had the same effect.

The presence of the mutation could be detected by means of molecular markers (the SNP marker that can be used for this purpose is presented as SEQ ID No. 2), and in flowering plants one could also use the flower color as a visual marker. Homozygous mutants have very pale (almost white) flowers than the flowers of wild-type and heterozygous plants, which are blue (FIG. 2).

The causal SNP mutation was detected by means of DNA-sequencing of a PCR-fragment of the OPR3 gene. First, a fragment of the endive OPR3 gene containing the SNP was amplified by PCR, using suitable PCR-primers that were designed based on the sequence information in SEQ ID No. 2. Subsequently, the DNA-sequence of the PCR product was determined by means of Sanger sequencing, using the following oligonucleotide as forward sequencing primer: GGCAAGTTCAATCTCTCTCAC (SEQ ID NO: 4). Of course various other techniques can also be used for the detection of the SNP in SEQ ID No. 2.

Example 4

Transfer of the Reversible Male Sterility Trait to Another *Cichorium* Plant

The deposited endive seeds harboring the trait of the invention (deposited as NCIMB number 42092) have been produced by allowing endive plants homozygous for the reversible male sterility trait to be pollinated by bumblebees, with pollen from endive plants heterozygous for the reversible male sterility trait. The latter plants are fully male fertile. Of the seeds resulting from this cross about 50% were homozygous for the trait of the invention, and about 50% were heterozygous for the said trait.

Endive plants of the invention were crossed with wild-type (WT) endive plants, which do not carry the trait of the invention. Plants grown from seeds of the deposit were first selected (phenotypically on the basis of male sterility and/or a pale flower color, and/or on the presence of the causal SNP mutation in the OPR3 gene in a homozygous state), to ensure that the trait of the invention would be transferred to the F1 generation in 100% of the cases. Alternatively, this selection can be done in the F2 generation, although this is less efficient.

The F1 plants resulting from this cross had the same phenotype as the wild-type plant, i.e. they displayed normal fertility and a normal, blue flower color. Nevertheless, the presence of the trait of the invention in a heterozygous state could be detected by means of a molecular marker. The SNP that can be used for this purpose is presented as SEQ ID No. 2. This molecular marker can be used to identify the presence of the genetic determinant that underlies the trait of the invention in endive plants grown from seeds as deposited under NCIMB number 42092.

In the F2 generation the trait of the invention is segregated in a manner that corresponds with a monogenic recessive inheritance. The trait of the invention could be introduced into a wild-type endive plant by crossing the wild-type endive plant with an endive plant of the invention and after selfing for the desired phenotype in the F2 generation, for example by selection on male sterility and/or the presence of the molecular marker in a homozygous state. The latter method of detection has the advantage that plants of the invention can be identified at a young developmental stage, long before they start flowering.

In the F2 generation the male sterility trait was also reversible. The addition of jasmonic acid and/or one or more jasmonic acid derivatives, in particular methyl jasmonate, was sufficient to restore male fertility, as described in Example 3.

In a similar manner the trait of the invention can also be introduced into e.g. witloof or radicchio plants (*Cichorium intybus*).

The invention is further described by the following numbered paragraphs:

1. Plant of the Compositae family exhibiting a reversible genic male sterility trait, characterised in that the genic male sterility is caused by a reduction or complete absence of endogenous jasmonic acid production, resulting from interference with one or more target genes involved in endogenous jasmonic acid production, selected from the group consisting of lipoxygenase, allene oxide synthase, allene oxide cyclase and 12-oxo-phytodienoic acid-10,11-reductase, or their functional homologues.

2. Plant of paragraph 1, wherein the male sterility can be reversed by the application of jasmonic acid and/or one or more jasmonic acid derivatives, in particular methyl jasmonate.

3. Plant of paragraph 1 or 2, wherein the interfering with the one or more target genes consists of preventing transcription thereof.

4. Plant of paragraph 3, wherein transcription is preferably prevented by means of RNA oligonucleotides, DNA oligonucleotides or RNAi molecules directed against the target gene promoter, or wherein transcription is preferably prevented by means of the expression of a negatively acting transcription factor acting on the target gene promoter.

5. Plant of paragraph 1 or 2, wherein the interfering with the one or more target genes consists of destabilising the target gene mRNA or transcript, preferably by means of nucleic acid molecules that are complementary to the target gene mRNA or transcript, selected from the group consisting of antisense RNA, RNAi molecules, Virus-Induced Gene Silencing (VIGS) molecules, co-suppressor molecules, RNA oligonucleotides or DNA oligonucleotides, or wherein the interfering with the one or more target genes consists of inhibiting the target gene expression product, preferably by means of the expression product(s) of one or more dominant-negative nucleic acid constructs, or preferably by means of one or more chemical compounds.

6. Plant of paragraph 1 or 2, wherein the interfering with the one or more target genes consists of the introduction of one or more mutations into the target gene, leading to perturbation of its biological function, and wherein the one or more mutations are preferably introduced randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements, and/or wherein the one or more mutations are introduced specifically by means of homologous recombination or oligonucleotide-based mutation induction.

7. Plant of any one of the paragraphs 1-6, wherein the plant is a plant of the genus *Lactuca*.

8. Plant of paragraph 7, wherein the plant is a plant of the species *Lactuca sativa*, and wherein the male sterility trait is caused by a genetic determinant, which is as present in the genome of plants grown from seed of which a representative sample was deposited with the NCIMB under accession number NCIMB 42060, in which the presence of the said genetic determinant can be identified by a molecular marker characterised by SEQ ID No. 1.

9. Plant of the Compositae family of any one of the paragraphs 1-6, wherein the plant is a plant of the genus *Cichorium*.

10. Plant of paragraph 9, wherein the male sterility trait is caused by a genetic determinant, which is as present in the genome of plants grown from seed of which a representative sample was deposited with the NCIMB under accession number NCIMB 42092, in which the presence of the said genetic determinant can be identified by a molecular marker characterised by SEQ ID No. 2.

11. Plant of paragraphs 9-10, wherein the homozygous presence of the genetic determinant underlying the male sterility trait can be identified by a pale flower colour, when compared to plants not having the said genetic determinant, or to plants in which the said genetic determinant is present in a heterozygous state.

12. Use of the plant of paragraphs 7-8 as a female parent for the creation of hybrid *Lactuca* seeds.

13. Use of the plant of paragraphs 9-11 as a female parent for the creation of hybrid *Cichorium* seeds.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Cichorium* plant comprising a reversible genic male sterility trait, wherein the genic male sterility is caused by a genetic determinant, which is as present in the genome of plants grown from seed of which a representative sample was deposited with the NCIMB under accession number NCIMB 42092, and wherein said genetic determinant is the C to A SNP mutation in SEQ ID NO: 2 of exon 2 of the 12-oxo-phytodienoic acid-10,11-reductase (OPR3) gene.

2. The plant as claimed in claim 1, wherein the homozygous presence of the genetic determinant underlying the male sterility trait can be identified by a pale flower color, when compared to plants not having the said genetic determinant, or to plants in which the said genetic determinant is present in a heterozygous state.

3. The plant as claimed in claim 1, wherein the male sterility can be reversed by applying jasmonic acid and/or methyl jasmonate.

* * * * *

SEQUENCE LISTING

```
<160> NUMBER OF SEQ ID NOS: 4

<210> SEQ ID NO 1
<211> LENGTH: 1823
<212> TYPE: DNA
<213> ORGANISM: Lactuca sativa

<400> SEQUENCE: 1
atggctgaaa caccgccgtc tgccgacaat ccaactctct tttctccatt caagatgggc      60
aagtttaatc tctctcacag gtccgttgtt tctatccttt ctttctcttca ctttctaatc     120 ataaatccgt cccccctata aaagtccttc agattttgag cttgatccag tcttgaccga     180
tcactatacc gtgttttggt tgtagggtgg tgttagctcc gatgacgcgg tgtagggcgt     240
taaatagcat accgaatcaa gctctggtgg agtattacag gcagagagca accgccggtg     300
ggtttctcat cacggagggg acaatgatct ctcctacctc cgccgggtaa tttcgctatt     360 cctttgttc ttcaagggtg ttttagtaaa tcaacattcc aacataattc accgggacaa     420
accatataaa accgccacgt ggcaattctt agttccttac atagtgcttt gtgggacctg     480
cagtatagac tattattaaa gtcacaccat tattaaagtc acattctctt tataaccact     540
ttataaagtc tttataacta aaaaatgtgt tttttttcgtt gtactttata gttagattag     600
atgcataatg tggatcttat gaaccattaa acaatgatac aagctacttg tgttctaaag     660
```

```
ttaaagatgc catttgatt cttaatttaa aaaacccatt tggtttagga ataccccttt      720
attcatcgat cattataaag cccaaattaa cgatctttct ggtaaaaaaa aacccaattt      780
ggtgatcagg ttccctcacg taccaggtat atttaatcaa gaacaagttg aagcttggaa      840
gaaagtcgtg gatgcagttc atgaaaaagg cgctgtgatc ttttgttaat tatggcatgt      900
cggcagagca tcccaccaag gtacgctttc ttccatctaa aagtctcaaa atctcaacat      960
tttgattttt gaacctaaat tcgatcgaa agtgatcatt gtgttaaca aacagtatat     1020 caacctaatg gggttgcacc aatatcatct acaagcaaac ccatatcgaa aaatggaga     1080 attttaatgc ccgatgggac ccacgctcaa tatccaaacc ctcgaccact cgctacccat     1140
gaaataccag aggtggtgga agactatcgt ctggcagcaa ttaacgccat tgaagcaggt     1200
tttgatggaa tcgagattca cggagcccat ggttatcttc tcgatcaatt catgaaagat     1260
ggcatcaata atcgaaccga tgaatatggt ggatctttag caaaccgatg caaattctta     1320
ctgaaagtgg tgaaatcgat agctacagcc attggtgcag ataaagtcgg tgttagaatc     1380
tcaccagcta ttgaccattt agacgccatg gattctgacc cacgtagctt agggcttgaa     1440
gtaattgaaa gactgaataa acttcaggtt gaattagggt caaagttgac ttatcttcat     1500
gtgactcaac caaggtacac ggcttatggt caaacagaag ctggaagcca tggaagtgaa     1560
gaggaagttg ctgagttgat gaagatatgg agaagggcat ttatgggaac ttttgtttgt     1620
agtggtgggt atactagaga gcttgggatt gaagctgtgg ctaaaggga tgctgatttg     1680 gtggcttatg gaaggctttt tatatcgaat ccggatttgg ttttgagact caaggttaat     1740
gcacctttga ataggtatgt tagggctagt tttatacac atgatcctgt tgtagggtac     1800
actgattacc cttcacttga gaa                                            1823

<210> SEQ ID NO 2
<211> LENGTH: 289
<212> TYPE: DNA
<213> ORGANISM: Cichorium endivia

<400> SEQUENCE: 2
tcaacatcca gatctccgat cccaagcaaa taatggctga aacgacgccg tctgccgaca       60
atccaaccct cttttctccg tacaagatgg gcaagttcaa tctctctcac agggtgatca      120
gttactttac ttcgatccat tgttctcgca gctttctgat catacttcat tcccccagca      180
aaataattca gaatttgacc ttgatccaat tctgttttta attcttttac cgattagttc      240
accgtgtttt ggttgtaggg tggtgttagc tcagatgacg agatgcagg                  289

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcttggaaga aagtcgtgga tg                                                22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
    primer

<400> SEQUENCE: 4
ggcaagttca atctctctca c                                              21
```